United States Patent [19]
White

[11] Patent Number: 5,643,216
[45] Date of Patent: Jul. 1, 1997

[54] PATIENT BRACELET HAVING CATHETER CAPTURE INTEGRALLY FORMED THEREWITH AND METHODS OF MAKING THE SAME

[76] Inventor: James E. White, 4127 E. Churchill, Springfield, Mo. 65809

[21] Appl. No.: 476,845

[22] Filed: Jun. 8, 1995

[51] Int. Cl.[6] ............................................. A61M 25/00
[52] U.S. Cl. ........................... 604/174; 128/DIG. 26; 604/180
[58] Field of Search .................. 604/174, 178, 604/180; 128/DIG. 26, DIG. 15

[56] References Cited

U.S. PATENT DOCUMENTS

| | | | |
|---|---|---|---|
| 2,499,898 | 3/1950 | Anderson | 128/DIG. 15 X |
| 3,031,730 | 5/1962 | Morin | 128/DIG. 15 |
| 3,866,611 | 2/1975 | Baumrucker | 128/DIG. 15 X |
| 4,006,744 | 2/1977 | Steer . | |
| 4,197,720 | 4/1980 | Nani | 63/11 |
| 4,226,036 | 10/1980 | Krug | 40/21 C |
| 4,362,156 | 12/1982 | Feller et al. | 604/165 |
| 4,490,141 | 12/1984 | Lacko et al. | 604/180 |
| 4,585,443 | 4/1986 | Kaufman | 128/DIG. 26 X |
| 4,846,815 | 7/1989 | Scripps | 128/DIG. 15 X |
| 5,069,206 | 12/1991 | Crosbie | 128/DIG. 26 X |
| 5,084,026 | 1/1992 | Shapiro | 128/DIG. 26 X |
| 5,221,265 | 6/1993 | List | 604/180 |
| 5,292,312 | 3/1994 | Delk et al. | 604/180 |
| 5,304,146 | 4/1994 | Johnson et al. | 604/180 |
| 5,306,256 | 4/1994 | Jose | 604/180 |
| 5,308,337 | 5/1994 | Bingisser | 604/174 |
| 5,334,186 | 8/1994 | Alexander | 604/180 |
| 5,389,082 | 2/1995 | Baugues et al. | 604/180 X |

*Primary Examiner*—Sam Rimell
*Attorney, Agent, or Firm*—Richard L. Marsh

[57] ABSTRACT

A patient bracelet system is provided having at least one bracelet adapted to be worn about a portion of the lower arm of a patient wherein the bracelet has means to secure the bracelet about the arm. The securing means comprises a plurality of bulbous projections extending from one surface of one end of the bracelet and a plurality of grooves adapted for receiving the bulbous projections therein in at least one surface of the bracelet in an end opposite the first end, the grooves additionally being adapted to receive a portion of a medicant delivery system therein. In one embodiment, at least two bracelets are secured about the forearm in spaced relation one to the other by stay means, each of the stay means being adapted to be secured in at least one of the plurality of grooves in each of the bracelets.

20 Claims, 5 Drawing Sheets

PATIENT BRACELET HAVING CATHETER CAPTURE INTEGRALLY FORMED THEREWITH AND METHODS OF MAKING THE SAME

BACKGROUND OF THE INVENTION

1. Field of the Invention

This invention relates to a patient bracelet adapted to be worn about an appendage of the patient, such as the wrist, wherein the bracelet incorporates a means to capture and removably retain at least a portion of a medicant delivery system including items such as infusion plugs, catheter, cannulae or tubing associated with same to prevent movement of the catheter or cannula relative to the appendage of the patient.

2. Prior Art Statement

It is known to provide a bracelet for identification of a patient or for holding patient records having a plurality of perforations adjacent a first end and a rivet and rivet clinch in an opposite end for permanently attaching the first end to the second end. For instance, see the U.S. Pat. No. 4,226,036 issued on Oct. 7, 1980 to Albert E. Krug.

It is known to provide adhesive means for attaching cannulae to the skin of a patient. For instance, see U.S. Pat. No. 4,490,141 issued on Dec. 25, 1984 to Mark A. Lacko, et al.; U.S. Pat. No. 5,221,265 issued on Jun. 22, 1993 to Harald List; U.S. Pat. No. 5,292,312 issued on Mar. 8, 1994 to Robert E. Delk, et al.; and U.S. Pat. No. 5,304,146 issued on Apr. 19, 1994 to Melissa C. Johnson, et al.

It is also known to suture portions of a medicant system to the skin of the patient. For instance, see the U.S. Pat. No. 4,362,156 issued on Dec. 7, 1982 to John Feller, Jr., et al.

It is further known to provide a structure having inter-engageable ends to form band means. For instance, see U.S. Pat. No. 4,197,720 issued on Apr. 15, 1980 to James Nani.

It is further known to provide means for gripping a cannula in a mounting body having frictional engaging means comprising a knob frictionally fitted into an opening. The mounting body is adapted to be secured to the patient with adhesive means. For instance, see the U.S. Pat. No. 4,006,744 issued on Feb. 8, 1977 to Peter Leslie Steer.

Finally, it is known to provide a cannula tube clip device for attaching a cannula to the patient's garment and having a stud adapted to be frictionally fitted and retained in a slot. For instance, see the U.S. Pat. No. 5,308,337 issued on May 3, 1994 to Timothy A. Bingisser.

SUMMARY OF THE INVENTION

The prior methods of fixing portions of medicant delivery systems have obvious drawbacks. The adhesive means used to attach these portions to the patient cause discomfort and irritation to the patient and do not always hold the medicant delivery system fully in place. Small portions of the delivery system such as the scalp needle have heretofore required stitching the scalp needle set to the skin of the patient causing considerable discomfort and irritation. It is therefore, desired to avoid the use of adhesives in direct contact with the skin or the suturing of medicant apparatus to the skin of the patient in an effort to maximize patient comfort and minimize irritation to the patient's sensitive skin. The instant invention provides a means for securing portions of a medicant delivery system to an appendage of a patient to prevent movement of these portions of the delivery system relative to the appendage thereby preventing accidental removal of the cannulae from the patient, the means comprising an elongate member of given width and a length at least initially substantially greater than the circumference of the appendage, the elongate member having a first end and a second end, the first end having a plurality of projections extending from a first surface of the elongate member and the second end having a plurality of grooves of a shape complementary with the projections spaced in serial fashion on a second surface of the elongate member. The elongate member is adapted to encircle a portion of an appendage of the patient, such as an arm or a leg, with at least one of the projections being received in at least one of the grooves.

The means may be in the form of a bracelet with the plurality of projections extending along at least one surface of a first end of the bracelet in serial fashion with a distance between each of the projections approximately twice the distance between each of the grooves thereby permitting portions of a medicant delivery system to be placed in the intervening grooves of the bracelet, frictionally retaining the portions within the grooves of the bracelet.

Therefore, it is an object of this invention to provide a bracelet adapted to be worn about a portion of an appendage of a patient having means to secure the bracelet about the appendage wherein the means to secure the bracelet comprises a plurality of projections having spaces therebetween with the projections extending from at least one surface of a first end of the bracelet, and a plurality of grooves in an end opposite the first end, the grooves having teeth therebetween, wherein at least one of the grooves is adapted to receive at least one of the plurality of projections therein.

It is another object of this invention to provide a bracelet to be worn about a portion of an appendage of a patient having a plurality of projections extending along one surface of the first end of the bracelet in serial fashion with a distance between each of the projections being an integer multiple of the distance between each of the grooves.

It is another object of this invention to provide a bracelet to be worn about a portion of an appendage of a patient having a plurality of projections extending along one surface of the first end of the bracelet in serial fashion with a distance between each of the projections being approximately twice the distance between each of the grooves.

It is yet another object of this invention to provide a bracelet to be worn about a portion of an appendage of a patient having a plurality of projections wherein the projections have an enlarged end and an body portion wherein the enlarged end is larger in longitudinal cross section than the body portion.

It is yet another object of this invention to provide a bracelet to be worn about a portion of an appendage of a patient the bracelet having a plurality of projections wherein the projections have an enlarged end which is cylindrical and extends in length an amount substantially equal to the distance from one side edge of said bracelet to the opposite side edge thereof and is spaced a distance substantially equal to the diameter of the cylinder from one surface of the bracelet.

Still another object of this invention is to provide a bracelet to be worn about a portion of an appendage of a patient the bracelet having a plurality of projections and grooves therein where the grooves receive a portion of at least one medicant delivery system in the grooves which are unoccupied by one of said projections when the bracelet is secured about the appendage.

Still another object of this invention is to provide a bracelet to be worn about a portion of an appendage of a patient the bracelet having a plurality of projections and grooves therein where the grooves receive a portion of at least one cannula in the grooves which are unoccupied by one of said projections when the bracelet is placed about the appendage.

Still another object of this invention is to provide a bracelet to be worn about a portion of an appendage of a patient the bracelet having a plurality of projections and grooves therein where the grooves receive a portion of at least one infusion plug in the grooves which are unoccupied by one of said projections when the bracelet is placed about the appendage.

A further object of this invention is to provide a bracelet to be worn about a portion of an appendage of a patient, the bracelet having a plurality of projections and grooves therein where the grooves receive at least one rotation restrainer in grooves unoccupied by one of said projections when the bracelet is placed about the appendage.

An additional object of this invention is to provide a bracelet to be worn about a portion of an appendage of a patient, the bracelet having a plurality of grooves having teeth therebetween and wherein at least one of the teeth has a second groove disposed therein adapted to receive and retain scalp cannula or robing associated therewith.

Still another object of this invention is to provide a patient bracelet system comprising at least two bracelets each adapted to be worn about a portion of an appendage of a patient, each of the bracelets having means to secure the bracelet about the appendage, wherein the means to secure each bracelet comprises a plurality of projections extending from at least one surface of a first end of the bracelet, the projections having spaces therebetween; a plurality of grooves in an end opposite the first end, the grooves having teeth therebetween; at least one of the grooves adapted to receive at least one of the plurality of projections therein, and wherein the bracelets are disposed in spaced relation one from the other and secured in the spaced relation by stay means, each of the stay means being adapted to be secured in one of the plurality of grooves in each bracelet.

Finally, it is an object of this invention to provide a bracelet for securing medicant dispensing systems therein in an area adjacent a venipuncture site wherein the bracelet has patient information permanently printed thereon.

DESCRIPTION OF THE PREFERRED EMBODIMENTS

While the various features of this invention are hereinafter described and illustrated as a means to secure portions of a medicant delivery system to an appendage of a patient and in particular to secure cannulae or tubing associated therewith to the forearm of a patient adjacent a venipuncture site without placing adhesive means upon the skin of the patient, it is to be understood that the invention can be used for a variety of uses as hereinafter described.

Figures 1, 5:
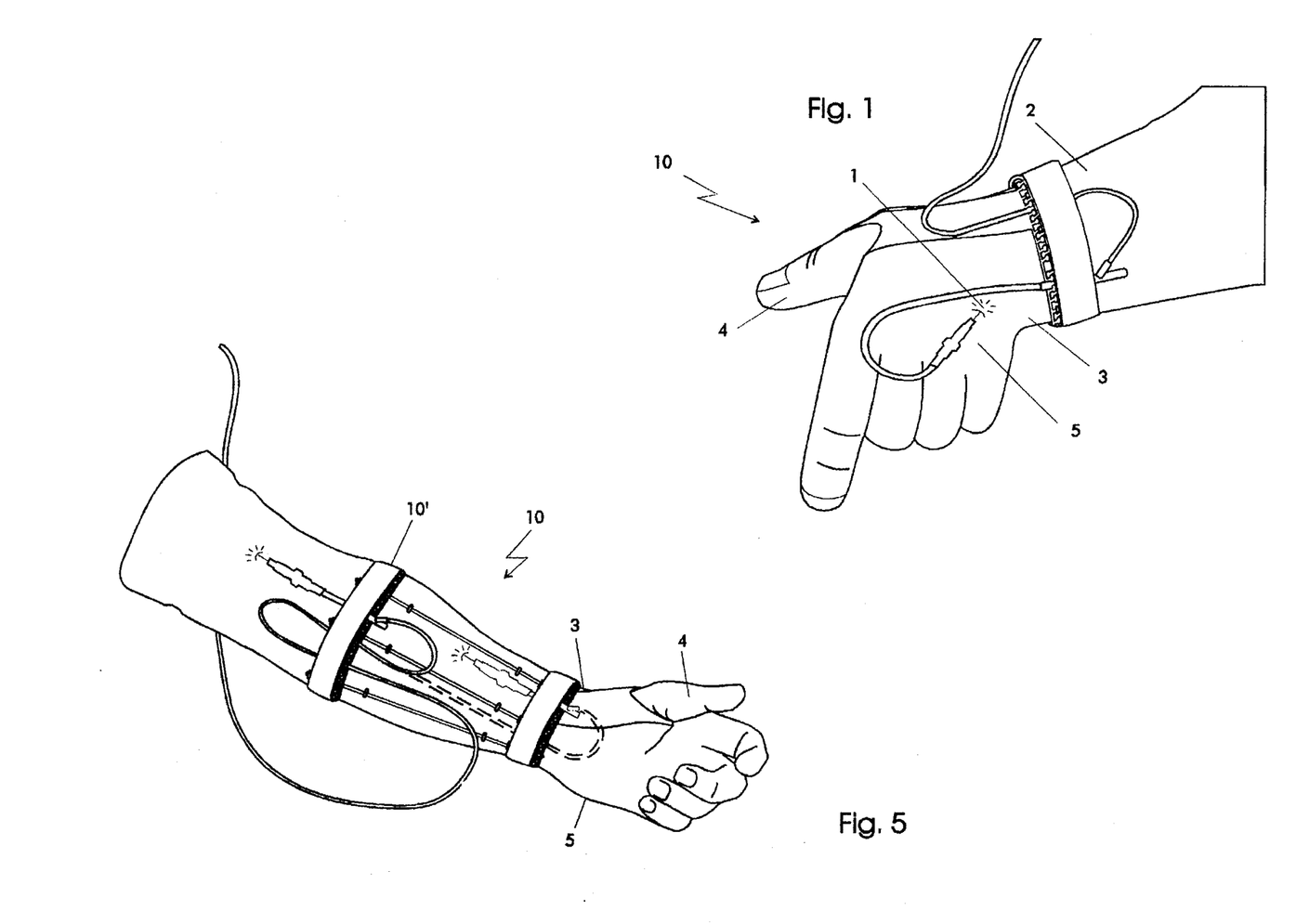
FIG. 1 is a perspective view of an embodiment of the bracelet of the invention fitted around the wrist of a patient.
FIG. 5 is a perspective view of a second embodiment of the invention fitted around the wrist and the upper forearm of a patient.

Referring now to FIG. 1, in the preferred embodiment of this invention, the bracelet, generally described by the numeral 10, is secured about an appendage 2 of a patient, such as wrist 3, adjacent a venipuncture site 1 in appendage 2. Bracelet 10 may have means to inhibit rotation about the wrist 3 comprising rotation restrainer 99 adapted to receive one of the digits 4 of the hand 5 of the patient in digit hole 100 as hereinafter described.

Figure 2:
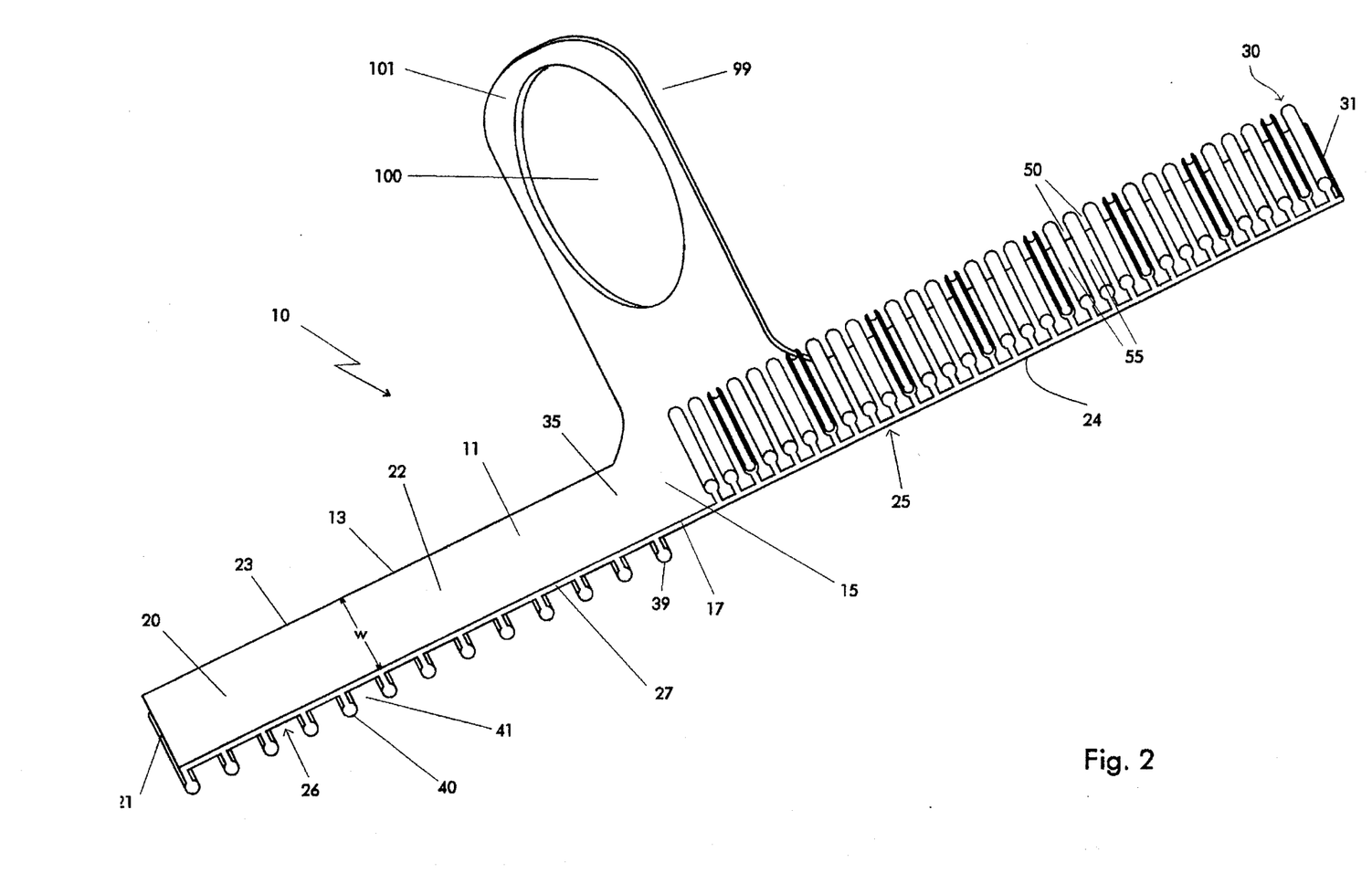
FIG. 2 is a perspective view of the preferred embodiment showing the bracelet in its elongate form with the first end separated from the second end.

FIG. 2 shows bracelet 10 as a flat elongate band 11 of width W having a first end 20, a medial portion 15 and a second end 30 opposite first end 20. Bracelet 10 further has inner surface 25 and opposite outer surface 35. First smooth portion 24 of inside surface 25 from terminal end 31 of second end 30 through medial portion 15 is adapted to be disposed against the skin of the patient when bracelet 10 is wrapped about appendage 2 as shown in FIG. 1. The remainder of inside surface 25 from medial portion 15 to opposite terminal end 21 has a plurality of projections 40 disposed seriatim thereon constituting a first part of the means to secure bracelet 10 about appendage 2. Projections 40, having spaces 41 therebetween, extend from underside 26 of end 20 and are disposed transverse the longitudinal extent of flat elongate band 11 in repeating serial fashion along underside surface 26. A second pan of the means to secure bracelet 10 about appendage 2 of the patient comprises a plurality of grooves 50, having teeth 55 therebetween, disposed in a portion of outer surface 35 of second end 30. Teeth 55 are shown extending from terminal end 31 through medial portion 15 but may extend to terminal end 21 of first end 20. At least one of grooves 50 is adapted to receive at least one of projections 40 therein thereby securing bracelet 10 to appendage 2. Preferably, several of projections 40 are received in several of grooves 50 as is readily apparent from a viewing of FIG. 8.

First smooth portion 24 of inner surface 25 of elongate band 11 is from two to twelve inches in length as measured from terminal end 31 to innermost projection 39. The preferred length is about nine inches in order that elongate band may encircle the wrist of an adult male without having either projections 40 or teeth 55 in contact with the skin of the patient. Terminal end 31 may be trimmed to a shorter length to accommodate the circumference of a smaller appendage such as the wrist of a child. For instance, terminal end 31 may be trimmed with surgical scissors to approximately five inches as measured from innermost projection 39 to newly created terminal end 31. Width W is preferably from about one-half inch to about one inch such that sufficient strength and stability is provided. The overall length of elongate band 11 is preferably about nineteen inches in length allowing same to encircle and be secured to the upper forearm of an adult.

Figure 3:
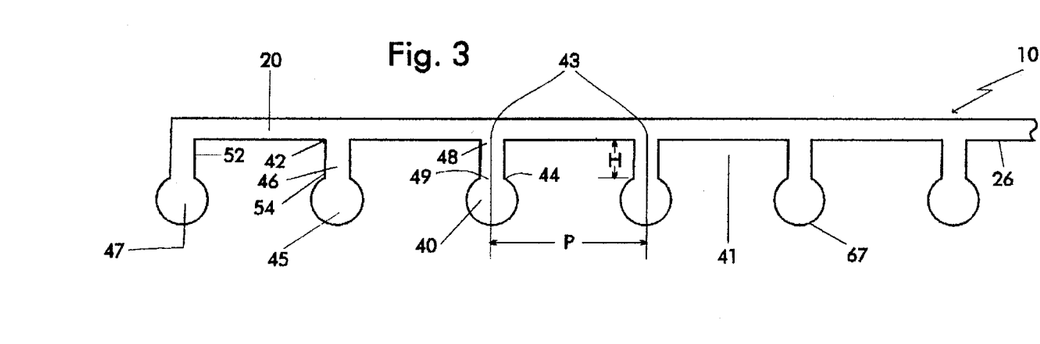
FIG. 3 is an enlarged view of the projections disposed on the first surface of the first end.
Figure 4:
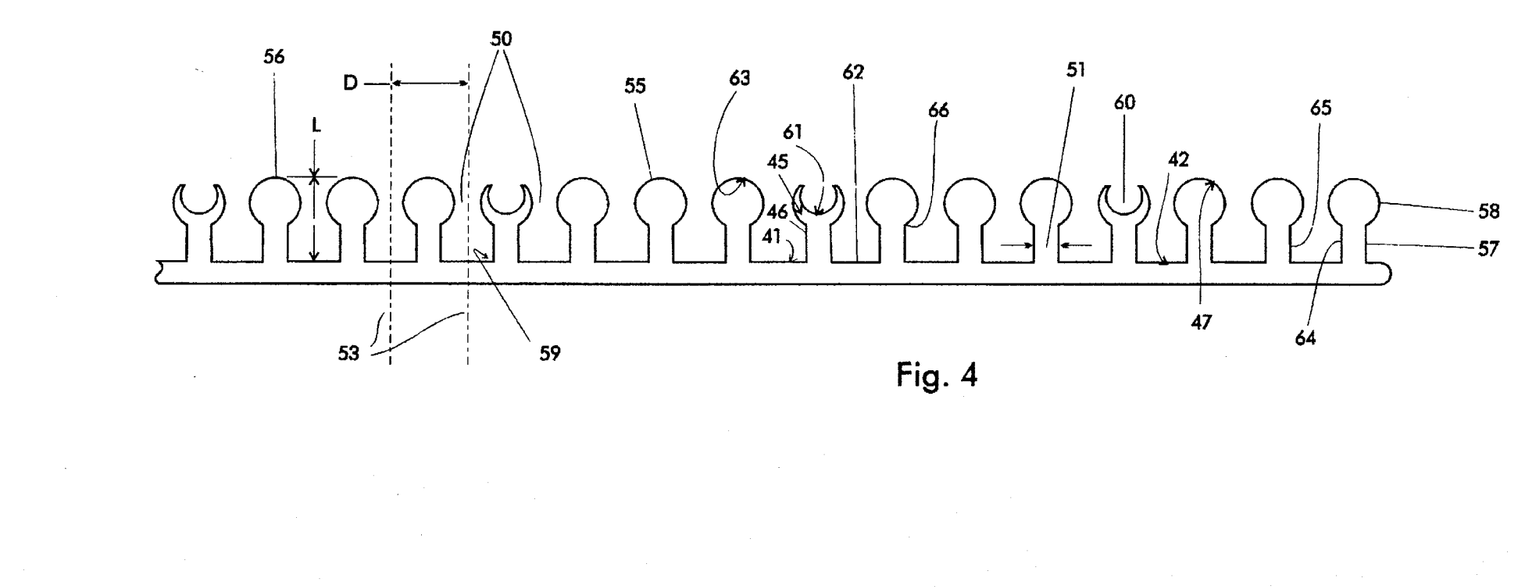
FIG. 4 is an enlarged view of the grooves disposed in the second surface of the second end.

Referring now to FIGS. 3 and 4, pitch P between center lines 43 of projections 40 is approximately twice distance D between center lines 53 of grooves 50. Projections 40 are substantially identical in shape as hereinafter described. Grooves 50 are also substantially identical in shape however, teeth 55 may further have small grooves 60 disposed in some of teeth 55 as will also be hereinafter described.

Figures 8, 9:
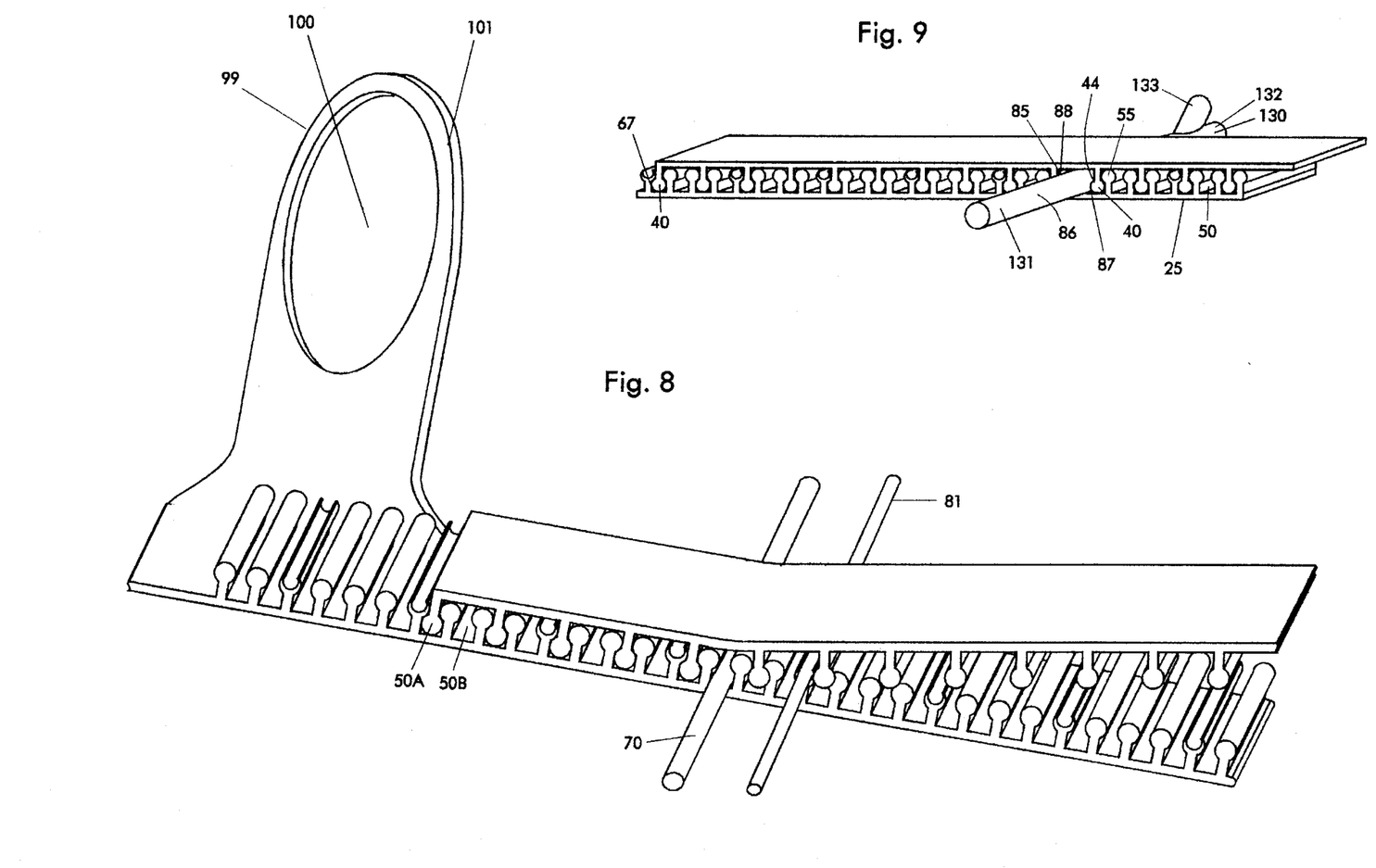
FIG. 8 is a perspective view of the bracelet of this invention having a portion of one end of the bracelet interconnected to the opposite end.
FIG. 9 is a partial perspective view of the bracelet of this invention showing an enlarged groove having an infusion plug inserted therein.

As is best seen in FIG. 8, every other groove 50A receives one of enlarged ends 45 of projections 40 therein leaving intervening groove 50B empty. Intervening grooves 50B are therefore free to accept portions of a medicant delivery system such as cannula tubing 70 therein for securing cannula tubing 70 to appendage 2 of the patient.

Referring again to FIGS. 3 and 4, cannula tubing 70 is typically 0.125" in outside diameter and therefore each of grooves 50 is approximately 0.125" wide as measured from opposing faces 64 and 65 of body portion 46. In this manner, cannula tubing 70 may be placed in at least one intervening grooves 50B of bracelet 10 and enlarged ends 45 of projections 40 in adjacent grooves 50 capturing cannula tubing 70 within bracelet 10. Capturing of cannula tubing 70 in bracelet 10 enhances patient comfort as entanglement of cannula tubing 70 is substantially reduced. Capturing of cannula tubing 70 adjacent venipuncture site 1 also facilitates observation of venipuncture site 1 by medical personnel. Cannula tubing 70 may be faked down in a series of reversing loops 140 as shown in FIG. 1 and FIG. 5 passing through more than one of intervening grooves 50B. Faking of cannula tubing 70 facilitates the capture of "Y" infusion plug 130 in a position immediately adjacent venipuncture site 1 for easy insertion of a second medicant. As is readily apparent to those skilled in the art, enlarged end 45 typically will be approximately 0.125" diameter making radius 47 approximately 0.0625".

Referring now to FIG. 4, projections 40 are substantially identical and have body portion 46 and enlarged end 45, body portion 46 being secured at one end 48 to underside 26 and enlarged end 45 being secured to and integral with opposite end 49. Body portion 46 is in the general shape of a rectangular parallelepiped and, as is readily apparent from a viewing of FIG. 2, extends from one side 23 to opposite side 27 of first end 20. Enlarged end 45 is in the general shape of a right circular cylinder extending a distance substantially equal to width W and having a portion of its outer surface integral with end 49 of body portion 46. Body portion 46 has a height H substantially equal to twice radius 47 of enlarged end 45 as measured from underside 26 to juncture 44 of enlarged end 45 with body portion 46. Body portion 46 may further be provided with fillet 42 of a radius not greater than radius 63 of outer portion 58 of teeth 55.

Grooves 50 are formed in outer surface 35 and have teeth 55 therebetween, grooves 50 being adapted to receive projections 40 of first end 20. As such, grooves 50 are shaped in cooperating fashion with projections 40 which will be best understood by describing the substantially identical teeth 55 therebetween. Teeth 55 have an inner portion 57 and an outer portion 58 wherein inner portion 57 has a medial thickness 51 substantially equal to distance D less twice radius 47 of projections 40. In this manner, when one of projections 40 is placed in one of grooves 50, it is held securely therein as there is little clearance between these mating parts. Typically, distance D is 0.187" making medial thickness 51 approximately 0.0625". Of course, medial thickness 51 may be larger or smaller in order to increase or decrease the rigidity of teeth 55. Grooves 50 may have a filet 59 disposed adjacent body portion 57 joining same with base 62 of groove 50. Filet 59 may have a radius 63 not greater than radius 47 of projections 40.

Grooves 50 have a depth L, measured from base 62 to outermost peripheral surface 56 of teeth 55, substantially equal to four times radius 47 of enlarged end 45. It is readily apparent, therefore, that when projection 40 is received in groove 50B, an inner-locking effect is achieved. This interlocking effect occurs became enlarged end 45, when received in groove 50A, is contiguous with base 62 and each of opposing side wall 64 and 65 of inner portions 57 of teeth 55 while resting beneath juncture 66 of outer portion 58 and inner portion 57. As cannula tubing 70 is substantially the same size as enlarged end 45, an interlocking effect also occurs wherein cannula tubing 70 is contiguous with surface 62, side walls 64 and 65 with its outer periphery captured immediately beneath juncture 66 of adjacent teeth 55.

A small groove 60 may be disposed in the outermost peripheral surface 56 of at least one of teeth 55 adapted to accept a smaller diameter cannula tubing such as used with a scalp vein set. Small groove 60 is disposed in such a manner that the small cannula tubing 81 of the scalp vein set is substantially tangent to a circle inscribing outermost peripheral surface 56. In this manner, small cannula tubing 81 is captured in small groove 60 and held therein by contact with underside 26 between projections 40. In a manner similar to cannula tubing 70, small cannula tubing 81 may also be faked down in a series of reversing loops 82 in a effort to minimize patient discomfort. Although small groove 60 is provided in the peripheral surface 56, it is fully understood that scalp needle tubing 81 may be captured between inner surface 62 and outer peripheral surface 67 of projection 40 or alternately between juncture 44 of projection 40 and juncture 66 of tooth 55 as scalp needle 81 is small in comparison to teeth 55 or projections 40. Finally, a small groove may be disposed in surface 62 such that scalp needle tubing 81 may be captured therein by outer peripheral surface 67 of projection 40.

In a typical intravenous (IV) tubing set, an "Y" infusion plug 130 is usually disposed near the catheter receiving end of the set. The "Y" infusion plug 130 is also usually of constant diameter throughout having a branch 133 of equal diameter. The diameter of the "Y" infusion plug 130 of a No. 1860 VENOSET®, manufactured by Abbott Laboratories, North Chicago, Ill., is approximately twice the diameter of cannula tubing 70 and therefore may also be captured and retained in bracelet 10 of the instant invention. Referring now to FIG. 9, when "Y" infusion plug 130 is desired to be placed adjacent venipuncture site 1 and retained in bracelet 10, an enlarged groove 85 is utilized to capture infusion plug 130 in second end 30 or in medial portion 15. Enlarged groove 85 may be molded into bracelet 10 or may be created by removing two adjacent teeth 55 from bracelet 10 utilizing a scalpel or surgical scissors by shearing off the teeth 55 substantially flush with base 62. In this manner, an enlarged groove 85 is created between two adjacent projections 40 at any location desire. One leg of "Y" infusion plug 130 can then be captured between base 62 and underside 26 in a manner similar to capturing cannula tubing 70 in groove 50B. For instance, when one leg 131 of "Y" infusion plug 130 is placed in enlarged groove 85, the adjacent remaining teeth 55 bear against the outer peripheral surface 67 of projections 40 which in turn bear against outer peripheral surface 86 of leg 131 of "Y" infusion plug 130. In this manner, leg 131 of "Y" infusion plug 130 is restrained from longitudinal movement relative to bracelet 10 by frictional contact with base 62 and underside 26. "Y" infusion plug 130 is further retained from transverse movement as outer peripheral surface 67 of one projection 40 near juncture 44 is in contact with outer peripheral surface 86 at a point 87 generally opposite a point 88 in contact with outer peripheral surface 67 of the next adjacent projection 40. As is readily apparent to one skilled in the art, "Y" infusion plug 130 is fully retained within enlarged groove 85 of bracelet 10 by frictional contact with four surfaces of enlarged groove 85. Of course, it is understood that any leg 131,132 or 133 may be captured in enlarged groove 85 or that more than one bracelet 10 may be utilized to capture more than one leg 131,132 and 133 of "Y" infusion plug 130. It is further understood, that, if desired, a separate infusion plug may be similarly captured in bracelet 10 in a manner similar to the capture of "Y" infusion plug as described above by removing an additional pair of adjacent teeth 55 in the preferred location.

Rotation restrainer 99 is best shown in FIG. 2. In the preferred embodiment, a loop 101 is integral with bracelet 10 and extends from one edge 13 in medial portion 15 of band 11 with digit hole 100 disposed therein. Loop 101 is of sufficient length to extend from wrist 3 around digit 4 and returning to one edge 13. Digit hole 100 is of sufficient size to accommodate a digit of the human hand such as the thumb. Although digit hole 100 is generally adapted to be utilized with the thumb, any other digit may be encircled by loop 101. Loop 101, in cooperation with inner surface 25 in contact with the skin of the patient, produces a rotation restrainer 99 to keep bracelet 10 in a fixed relationship with venipuncture site 1 to prevent damage to thereto.

An alternate or additional rotation restrainer 99' may be captured in grooves 50 in a manner similar to the capture of cannula tubing 70. The alternate rotation restrainer 99' shown in FIG. 10 has digit hole 100' disposed in an elongated loop 101' in a manner similar to rotation restrainer 99 however, alternate rotation restrainer 99' has a pair of extensions 102 forming ends 106 of loop 101', each extension 102 having a pair of first flanges 103 at outer end 107 thereof and a pair of second flanges 105 disposed on shank 104 between outer end 107 and cusp 106. The distance between each of first flanges 103 and each of second flanges 105 is substantially equal to width W of bracelet 10. When bracelet 10 is to be secured about wrist 3 of the patient, alternate rotation restrainer 99' is placed adjacent to a digit 4 in two grooves 50 spaced apart by a distance equal to a multiple of distance D. Shank 104 is the same diameter as cannula tubing 70 and is captured in grooves 50 by closure of projections 40 in adjacent grooves 50 as projections 40 cause teeth 50 to move slightly toward each other at the insertion of projection 40. Alternate rotation restrainer 99' and rotation restrainer 99 cooperate to place bracelet 10 in slight tension between said rotation restrainers 99' and 99 thereby positively preventing rotation of bracelet 10 in either direction.

Figures 7, 10:
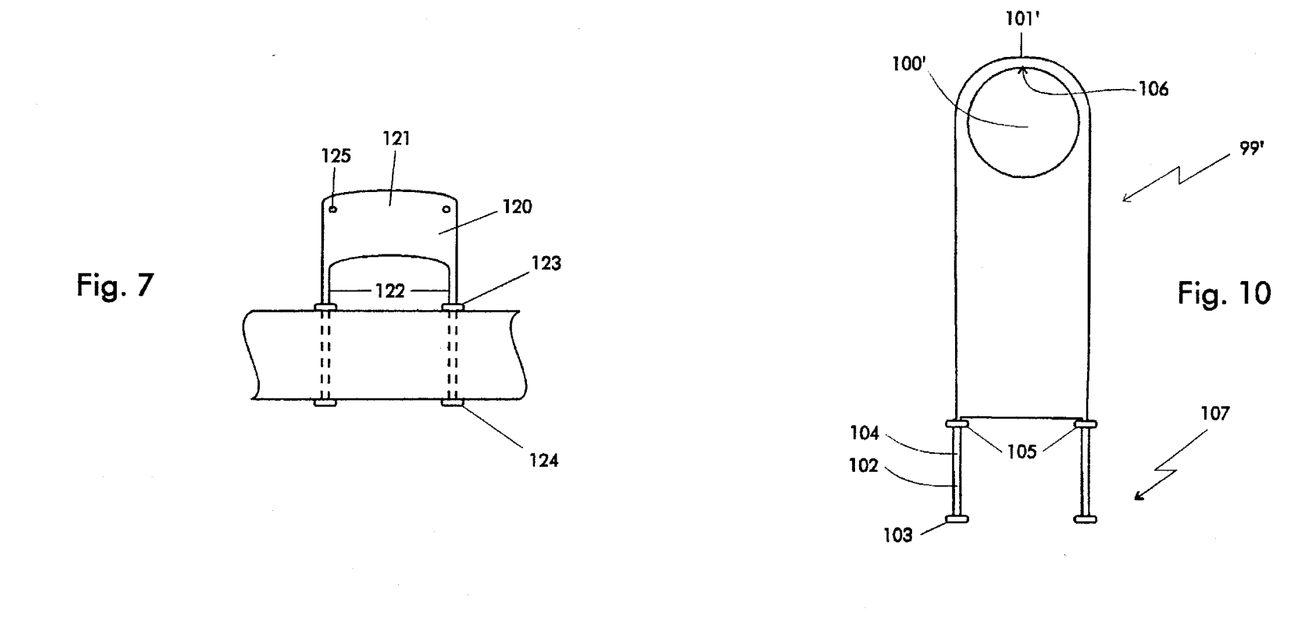
FIG. 7 is an enlarged view of a needle retaining butterfly adapted to be secured to the bracelet of the invention.
FIG. 10 is a plan view of an additional rotation restrainer adapted to be captured in the grooves of the bracelet of this invention.

In a like manner, a butterfly retainer 120 shown in FIG. 7 for a scalp needle attachment may be captured in grooves 50. Butterfly retainer 120 has an enlarged planar area 121 terminating in two elongated shank portions 122 spaced apart by a distance equal to a multiple of distance D. Each shank portion 122 has an inner flange 123 and an outer flange 124 spaced apart by a distance substantially equal to width W of bracelet 10. When butterfly retainer 120 is utilized, shanks 122 are placed in grooves 50 at the desired location with inner flange 123 on one side edge 33 or 37 of second end 30 and outer flange 124 on opposite side edge 37 or 33 respectively. Projections 40 are then inserted into grooves 50 adjacent shanks 122 causing teeth 55 to move slightly toward each other capturing shank portions 122 in grooves 50. Enlarged planar area 121 may have holes 125 disposed therein for suturing a scalp needle set to butterfly retainer 120 to avoid suturing the wings of the needle set directly to the skin of the patient as has been described in U.S. Pat. No. 4,362,156.

As is apparent to one skilled in the art, flat elongate band 11 is placed upon back 6 of wrist 3 of the patient with a digit 4, such as the thumb or other finger of the patient, extending through digit hole 100. First end 20 is wrapped in one direction about wrist 3 of the patient while second end 30 is wrapped in the opposite direction as a conventional bracelet is adapted to encircle wrist 3. Innermost projection 39 is placed in one of grooves 50 closest to the circumference of wrist 3 of the patient such that bracelet 10 provides the most comfort to the patient. Once bracelet 10 is secured as described, securing of a butterfly retainer 120, or attachment of a second rotation restrainer 99', insertion of an infusion plug 130, placement of rod stays 110 for another spaced apart bracelet 10 or securing of cannula tubing 70, 80 within bracelet 10 may proceed.

In the instance where a butterfly retainer 120 is desired to retain a needle set near bracelet 10, shank portions 122 between flanges 123 and 124 are placed in grooves 50 inboard of one groove 50 having innermost projection 39 therein such that the needle set is aligned with the location of venipuncture site 1. Therefore, grooves 50 inboard of one groove 50 having innermost projection 39 therein is understood to refer to those grooves 50 which are toward medial portion 15 of band 11. As recited above, shank portions 122 are spaced apart a distance equal to a multiple of pitch D and as such may have one or more projections 40 placed in grooves 50 between shank portions 122. If desired, the needle set may be sutured to butterfly retainer 120 by passing sutures through holes 125 in butterfly retainer 120 aligned with the holes in the needle set described in U.S. Pat. No. 4,362,156.

In the case of a particularly active patient, attachment of an additional rotation restrainer such as alternate rotation restrainer 99' may be desired. Shanks 102 of alternate rotation restrainer 99' are placed in grooves 50 at a distance apart from rotation restrainer 99 but at or near the location of another digit 4 of the patient which will be encircled by loop 101'. The distance from cusp 106 of digit hole 100' to side edge 27 of bracelet 10 facing away from hand 5 of the patient should be selected to allow bracelet 10 to be snugly retained in position upon insertion of second shank 102' into groove 50. Usually, alternate rotation restrainer 99' will be inserted after capture of cannula tubing 70, 80 or "Y" infusion plug 130. As can be readily appreciated, alternate rotation restrainer 99' is adapted to resist rotation of bracelet 10 in one circumferential direction while rotation restrainer 99 resists rotation of bracelet in an opposite circumferential direction thereby achieving the desired result.

Bracelet 10 further has a smooth portion 22 on outer surface 35 opposite surface 25 having projections 40 extending therefrom for the purpose of providing patient information. Patient information may be printed on, embossed upon, or engraved into bracelet 10 in smooth portion 22. Thermoplastic or elastomeric materials, as hereinafter described, which are suitable for bracelet 10 are particularly adapted to ink jet printing. Such patient information may include particular medicants prescribed or medical allergies as well as patient name, address and doctor. Once the patient has been admitted, bracelet 10 may then be secured around appendage 2 of the patient as is conventional in the admitting procedure. Since bracelet 10 is adapted to be opened by merely lifting end 31 from end 20 or medial portion 15 and decoupling each of projections 40 from grooves 50, bracelet 10 may be opened at a time when a medicant is required, the medicant system placed therein, secured thereto and bracelet 10 secured again about appendage 2 of the patient. Bracelet 10 may be opened repeatedly to provide additional medicant delivery systems or to change systems. Of course, for security reasons, innermost projection 39 may have a suitable adhesive applied to enlarged end 45 just prior to inserting innermost projection 39 into groove 50 closest to the circumference of wrist 3 of the patient. Pressure sensitive adhesive means such as cyanoacrylate adhesive are particularly suited for securing innermost projection 39 to groove 50. In this manner, bracelet 10 may be opened partially or fully for securing medicant delivery systems therein without completely removing bracelet 10 from appendage 2 of the patient thereby preserving previously secured delivery systems and/or patient information.

Figure 6:
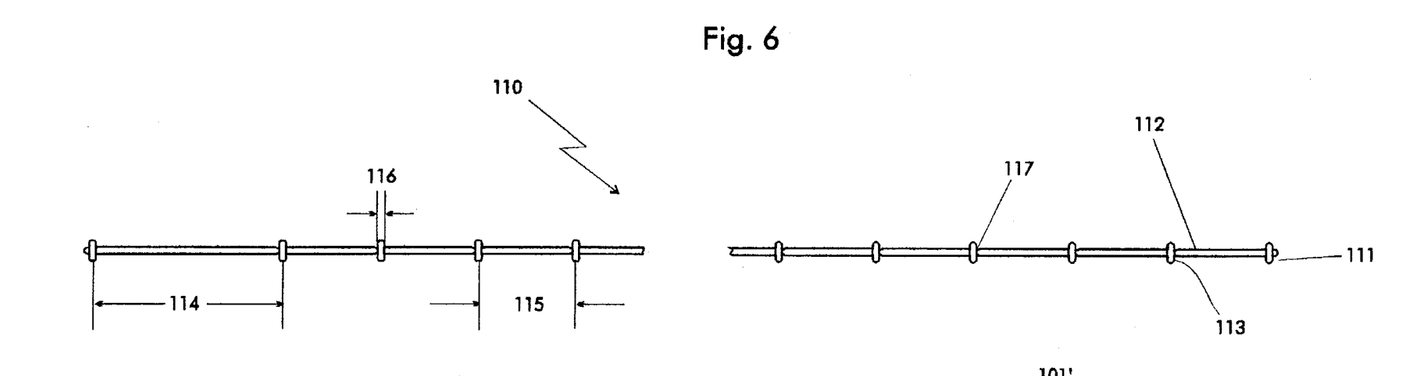
FIG. 6 is an enlarged view of the stay means separating the two bracelets of FIG. 5.

Referring now to FIG. 5, a second venipuncture site may be desired at a location on appendage 2 remote from wrist 3 for instance, in the forearm of the patient. In this instance, a second bracelet 10' is used which is spaced apart from bracelet 10 using rod stays 110 shown in FIG. 6. Each rod stay 110 has flanges 111 disposed upon shaft 112, flanges 111 being spaced apart by a distance 115 substantially equal to width W of bracelet 10 allowing second bracelet 10' to be spaced from bracelet 10 any multiple of width W plus thickness 116 of flange 111. An annular notch 117 placed adjacent each flange 111, is formed in shaft 112 such that rod stays 110 may be readily trimmed to the length necessary for spacing of bracelets 10 and 10'. Annular notch 117 provides a weakened area on shaft 112 allowing shaft 112 to be severed at annular notch 117 by breaking excess length from shaft 112 at the desired location.

Methods of making the various parts of the invention will now be described. Bracelet 10 may be injection molded from a suitable thermoplastic material such as vinyl, polyethylene, polyurethane, polyamide, polypropylene, polycarbonate, polyvinylchloride, polytetrafluoroethylene and the like or a suitable thermosetting elastomeric material and may further have a foamed elastomeric or thermoplastic material disposed on first smooth portion 24 of inner surface 25. Bracelet 10 may also be compression molded, extruded or machined from any one of these materials.

A preferred method of manufacture is to injection mold bracelet 10 in a multiple cavity mold to reduce the per part cost in a manner well known in the art. Each cavity in the mold would be a mirror image of one surface 25 or 35 of bracelet 10 with a mating half of the mold containing a mirror image of opposite surface 35 or 25 respectively with at least one of said halves having a recess for a portion of thickness 28 disposed therein. For instance, a mirror image of surface 25 may be machined into one mold half at a distance equal to thickness 28 from the mating line of the mold halves while the mirror image of surface 35 is machined into the other half of the mold with surface 35 contiguous with the mating line. Similarly, the mold halves may be made with only a portion of recess for thickness 28 disposed above the mirror image of respective surfaces 25 or 35 but the sum of the portions of the recess for thickness 28 disposed in each half totaling thickness 28. Each cavity of the multiple injection mold may be identical but may also be arranged in staggered fashion or inverted fashion to effectively utilize the available surface area of the mold and to provide for proper injection of the material. Bracelet 10 may have digit hole 100 and loop 101 molded integrally therewith by providing a cavity extension equal in thickness to thickness 28 machined into the surface of the mold and connected with the recess describing thickness 28 such that the material to be molded may flow therein uninhibited. A polyurethane material is preferred for bracelet 10 as polyurethane is pliable, readily molded and has a certain cohesion when fully molded which enhances the retention of the parts of the medicant system or additional parts of the invention constrained in bracelet 10.

In a similar manner, additional rotation restrainer 99' or butterfly retainer 120 may be molded or machined in the desired shape. A cavity is machined into a mold half of an injection mold substantially equal to the plan view shape of additional rotation restrainer 99' and at a thickness substantially equal to thickness 28. A first portion of the cavity is an annulus corresponding to loop 101' and second and third portions correspond to extensions 102. The second and third portions have an additional depth machined into the mold half corresponding to thickness 116 and shape of first flange 103 and second flange 105 respectively. The additional depth for first flange 103 and second flange 105 are disposed at a distance substantially equal to width W of bracelet 10. The second and third portions corresponding to extensions 102 are spaced at a distance substantially equal to a multiple of pitch D. An opposing half of the mold has second and third portions machined therein exactly mating with corresponding portions in the first half.

Butterfly retainer 120 is molded in identical fashion. Of course, rigid extensions 102 with first flange 103 and second flange 105 may be placed into the mold cavities having the remainder of butterfly retainer 120 or additional rotation restrainer 99' molded thereon. Furthermore, first flange 103 and second flange 105 may be washer like and be disposed in the recesses corresponding to these flanges and having the remainder of butterfly retainer 120 or additional rotation restrainer 99' molded thereon.

Rod stays 110 are preferably molded of a rigid material such as polycarbonate, polyvinyl chloride, polyamide, fiber filled polyamides or the like and are of extended length such that same are readily trimmed to the proper length upon use. The molding cavity for red stays 100 is similar to the mold cavity for extensions 122 of butterfly retainer 120 or extension 102 of additional rotation restrainer 99' but have a restriction immediately adjacent each recess corresponding to annular flange 111 for the molding of multiple flanges upon shaft 112. The molding cavity for rod stays 110 has repeating recesses spaced apart at a pitch distance 115 corresponding to width W of bracelet 10 plus thickness 116 of flange 111. The restriction is frustroconical in shape having its smaller end contiguous with each annular flange 111 on one side 113 thereof. The restriction in the molding cavity creates annular notch 117 on shaft 112 immediately adjacent each annular flange 111. Annular notch 117 facilitates trimming rod stay 110 to the length desired by breaking shaft 112 at annular notch 117. Alternately, rod stays 110 may be molded as shown in the left hand portion of FIG. 6 wherein pairs of flanges 111 are spaced apart by a distance 115 corresponding to width W of bracelet 10 plus thickness 116 of flange 111. Each pair of flanges is then spaced apart a distance 114 greater than distance 115. For instance, distance 114 may be in multiples of one inch whereas thickness 116 equals 0.125 inches and width W equals 0.500 inches.

While the forms and methods of this invention now preferred have been illustrated and described as required by the Patent Statute, it is to be understood that other forms and methods can be utilized and still fall within the scope of the appended claims.

What I claim is:

1. In a bracelet adapted to be worn about a portion of an appendage of a patient said bracelet having means to secure said bracelet about said appendage, the improvement wherein said means to secure said bracelet comprises a plurality of projections having spaces therebetween, said plurality of projections extending from at least one surface of a first end of said bracelet and along said at least one surface in serial fashion thereof, and a plurality of grooves in an end opposite said first end, said grooves having teeth therebetween, said plurality of projections having a distance therebetween approximately twice the distance between each of said grooves, wherein at least one of said grooves is adapted to receive at least one of said plurality of projections therein.

2. A bracelet as described in claim 1 wherein each of said plurality of projections have an enlarged end and a body portion wherein said enlarged end is larger in longitudinal cross section than said body portion.

3. A bracelet as described in claim 2 wherein said enlarged end is spherical.

4. A bracelet as described in claim 2 wherein said enlarged end is cylindrical and extends from one side edge of said bracelet to the opposite side edge thereof.

5. A bracelet as described in claim 1 wherein said grooves are adapted to receive a portion of a medicant delivery system therein in said grooves unoccupied by one of said projections.

6. A bracelet as described in claim 5 wherein said medicant delivery system is fixedly retained in said grooves when said bracelet is disposed about said appendage.

7. A bracelet as described in claim 1 wherein said grooves have a lower portion and an upper portion, said lower portion having a longitudinal cross section in the shape of a segment of a circle.

8. A bracelet as described in claim 1 wherein at least one of said teeth disposed between each of said grooves has at least one second groove disposed in an upper surface thereof contiguous with an opposing surface portion of said one end of said bracelet in said space disposed between said projections when said bracelet is disposed about said appendage.

9. A bracelet as described in claim 8 wherein each said second groove is adapted to receive and fixedly retain at least one scalp cannula therein.

10. A bracelet as described in claim 9 wherein each said second groove has a longitudinal cross section in the shape of a segment of a circle having a diameter smaller than the outside diameter of said scalp cannula.

11. A bracelet as described in claim 4 wherein said projections have a longitudinal cross sectional shape identical to said teeth.

12. A bracelet as described in claim 1 wherein means for displaying patient information is provided on a smooth surface opposite said surface having projections thereon.

13. A bracelet as described in claim 12 wherein said patient information is printed upon said smooth surface.

14. A bracelet as described in claim 1 wherein said bracelet has a rotation restrainer associated therewith to resist rotation of said bracelet during movement of the appendage.

15. A bracelet as described in claim 14 wherein said rotation restrainer is an integral part of said bracelet extending from one edge of said bracelet in a medial portion thereof.

16. A bracelet as described in claim 15 wherein said rotation restrainer is adapted to receive at least one digit of a hand of a patient in a digit hole disposed in said rotation restrainer.

17. A bracelet as described in claim 14 wherein said rotation restrainer is initially separate from said bracelet and is secured to said bracelet in at least one of said grooves between said grooves receiving said projections therein.

18. In a patient bracelet system comprising at least two bracelets each adapted to be worn about a portion of an appendage of a patient, each of the bracelets having means to secure the bracelet about the appendage, the improvement wherein said means to secure each bracelet comprises a plurality of projections extending from at least one surface of a first end of the bracelet, said projections having spaces therebetween; a plurality of grooves in an end opposite said first end, said grooves having teeth therebetween, at least one of said grooves adapted to receive at least one of said plurality of projections therein, and wherein said bracelets are disposed in spaced relation one from the other and secured in said spaced relation by stay means, each said stay means being adapted to be secured in one of said plurality of grooves in each bracelet.

19. A patient bracelet system as described in claim 18 wherein said plurality of projections extend along said at least one surface of a first end of said bracelet in serial fashion with a distance between each of said projections being approximately twice the distance between each of said grooves.

20. In a means for securing a portion of a medicant delivery system to an appendage of a patient to prevent accidental removal of the system from the patient, the improvement comprising an elongate member of given width having a first end and a second end, said first end having a plurality of projections extending from a first surface of said elongate member and said second end having a plurality of grooves in a second surface opposite said first surface, said grooves being of a shape complementary to said projections wherein said elongate member is adapted to encircle a portion of the appendage of the patient with at least two of said projections being received in at least two of said grooves wherein said plurality of projections extend along said first surface of said first end in serial fashion and said grooves extend along said second surface in serial fashion wherein the distance between each of said projections is approximately twice the distance between each of said grooves.

* * * * *